United States Patent
Feng et al.

(10) Patent No.: US 9,861,694 B2
(45) Date of Patent: Jan. 9, 2018

(54) EGFR ANTAGONIST FOR THE TREATMENT OF HEART DISEASE

(71) Applicants: Qingping Feng, London (CA); Xiangru Lu, London (CA)

(72) Inventors: Qingping Feng, London (CA); Xiangru Lu, London (CA)

(*) Notice: Subject to any disclaimer, the term of this patent is extended or adjusted under 35 U.S.C. 154(b) by 73 days.

(21) Appl. No.: 14/559,598

(22) Filed: Dec. 3, 2014

(65) Prior Publication Data
US 2015/0147386 A1 May 28, 2015

Related U.S. Application Data

(63) Continuation of application No. 13/825,605, filed as application No. PCT/CA2011/001301 on Nov. 30, 2011, now abandoned.

(60) Provisional application No. 61/418,075, filed on Nov. 30, 2010.

(51) Int. Cl.

| | |
|---|---|
| *A01N 43/00* | (2006.01) |
| *A61K 31/33* | (2006.01) |
| *A61K 39/395* | (2006.01) |
| *A61K 31/517* | (2006.01) |
| *A61K 31/5377* | (2006.01) |
| *A61K 31/7105* | (2006.01) |
| *A61K 31/713* | (2006.01) |
| *A61K 45/06* | (2006.01) |
| *C07K 16/28* | (2006.01) |
| *A61K 38/05* | (2006.01) |
| *A61K 9/127* | (2006.01) |
| *A61K 38/00* | (2006.01) |
| *A61K 39/00* | (2006.01) |

(52) U.S. Cl.
CPC .......... *A61K 39/3955* (2013.01); *A61K 9/127* (2013.01); *A61K 31/517* (2013.01); *A61K 31/5377* (2013.01); *A61K 31/713* (2013.01); *A61K 31/7105* (2013.01); *A61K 38/005* (2013.01); *A61K 38/05* (2013.01); *A61K 45/06* (2013.01); *C07K 16/2863* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,481,759 B2* | 1/2009 | Whitehurst et al. | 600/3 |
| 8,198,266 B2* | 6/2012 | Tharaux et al. | 514/183 |
| 2009/0202529 A1* | 8/2009 | Threadgill et al. | 424/133.1 |
| 2010/0310503 A1* | 12/2010 | Li | A61K 31/38 424/85.2 |

FOREIGN PATENT DOCUMENTS

WO  WO 2006042313 A2 *  4/2006

OTHER PUBLICATIONS

Fedak et al., "TIMP-3 deficiency leads to dilated cardiomyopathy," Circulation, Oct. 19, 2004; 110(16):240-9 (cited in IDS).*
Defazio et al., "Circulatory Changes in Acute Glomerulonephritis," Circulation, 1959;20:190-200.*
Athyros et al., "Effect of statins and ACE inhibitors alone and in combination on clinical outcome in patients with coronary heart disease."*
Farsaei et al., "Potential role of statins on wound healing: review of the literature."*
Tang et al., "Atorvastatin Therapy during the Peri-Infarct Period Attenuates Left Ventricular Dysfunction and Remodeling after Myocardial Infarction."*
NCT00134550.*

* cited by examiner

*Primary Examiner* — Jared D Barsky
(74) *Attorney, Agent, or Firm* — Eduardo Krupnik

(57) ABSTRACT

The present invention relates to the use of epidermal growth factor receptor (EGFR) antagonists in methods and compositions useful for the treatment of heart disease in a subject. In one embodiment, the methods of the present invention comprise: (a) administering to the subject an EGFR antagonist; and (b) inhibiting or substantially inhibiting the EGFR signal transduction cascade. In another embodiment the method of the present invention may be used in combination with another heart disease therapy.

14 Claims, 6 Drawing Sheets

EGFR ANTAGONIST FOR THE TREATMENT OF HEART DISEASE

CROSS REFERENCE TO RELATED APPLICATIONS

This application is a continuation of U.S. patent application Ser. No. 13/825,605 filed May 16, 2013, which in turn is a national stage application under 35 U.S.C. 371 of International Application No. PCT/CA2011/001301, filed Nov. 30, 2011, which in turn claims the benefit under 35 U.S.C. 119(e) of U.S. Provisional Application Ser. No. 61/418,072, filed Nov. 30, 2010, the contents of each of which are hereby incorporated by reference into the present disclosure.

FIELD OF THE INVENTION

The present invention relates to epidermal growth factor receptor antagonists. More particularly, the present invention relates to use of epidermal growth factor receptor antagonists in methods and compositions for treating heart disease, and for treating, preventing or minimizing conditions, diseases or disorders arising as a complication of heart disease.

BACKGROUND OF THE INVENTION

Cardiovascular diseases account for 12 million deaths annually worldwide and myocardial infraction (MI) is a leading cause of morbidity and mortality. Cardiac rupture, ventricular arrhythmia and heart failure are common causes of morbidity and mortality following MI. Cardiac rupture refers to a rupture of the left ventricle of the heart, generally following an acute myocardial infarction. Left untreated, the condition usually is fatal immediately or within a few days depending on the extent of the rupture. It is believed that such rupture occurs in approximately 10% of patients with fatal acute myocardial infarction [38]. Myocardial rupture causes 25,000 deaths a year in the United States alone and is the second most common cause of the death after an acute myocardial infarction.

Clinical studies have shown that incidence of cardiac rupture occurs in about 4-10% of all patients admitted with an acute MI, but is responsible for 12% of in-hospital mortality after thrombolytic therapy [1, 17, 28, 38]. Post-mortem examinations showed cardiac ruptures in 31-65% of patients who died of acute MI [18, 27]. Thus understanding the underlying mechanisms that lead to cardiac rupture will aid in the development of drugs that will decrease mortality following MI.

The myocardial extracellular matrix (ECM) plays an important role in maintaining the integrity and function of the heart [9]. The major constituents of the myocardial ECM are the fibrillar collagens composed of the tensile collagen I (about 80%), which is crucial for coordinating contraction, and collagen III (about 10%) which provides elasticity [3, 9]. Fibrillar collagens are synthesized as precursor peptides that are proteolytically cleaved at the amino- and carboxy-terminals before being inserted into the nascent fibrils [3]. One of the major inducers of collagen expression and synthesis by fibroblasts is the transforming growth factor-beta (TGF-β) [3]. Remodeling of the ECM is mediated by the matrix metalloproteinases (MMPs) and their endogenous inhibitors, the tissue inhibitors of metalloproteinases (TIMPs) [2]. An imbalance between the activities of MMPs and TIMPs can impair infarct healing and result in cardiac rupture [16, 30, 39].

TIMPs appear to be a family of 4 homologous proteins all of which are expressed in the heart [9]. Unique among the TIMPs, TIMP-3 (metalloproteinase inhibitor 3) is ECM bound, a potent inhibitor of all known MMPs, and is expressed at high levels in the healthy heart. However, in the diseased heart, TIMP-3 expression is reduced in association with maladaptive myocardial remodeling in patients with congestive heart failure [7]. Furthermore, loss of TIMP-3 expression in aged mice triggers progressive myocardial remodeling and dysfunction even in the absence of imposed stresses or injuries [8]. In humans, the TIMP3 gene that encodes for the metalloproteinase inhibitor 3 appears to be located on chromosome 22.

Maladaptive left ventricular remodeling has been consistently associated with a poor prognosis in patients after MI and in patients with chronic heart failure [39].

Following MI, cardiac fibroblasts initially repopulate the injured area through chemotaxis. This is followed by increased proliferation and differentiation into myofibroblasts, and formation of a granulated scar [3]. Subsequently, remodeling of the ECM occurs and ultimately leads to the formation of a mature scar tissue which is composed of collagen, fibroblasts, newly formed capillaries, and macrophages [4, 31]. TIMP-3 is a potent inducer of cardiac fibroblast proliferation [23]. Furthermore, a recent study showed that incidence of pericardial bleeding, indicative of cardiac rupture, was increased in TIMP-3$^{-/-}$ mice post-MI [32], suggesting a potential role of TIMP-3 in infarct scar healing.

Early post-infarct adaptation of the heart could be beneficial and promote survival, however, with deleterious long-term haemodynamic consequences. Long term progressive remodeling of the left ventricle with increases in the ventricular cavity size can occur up to 2 years post-infarct and it may be associated with increased cardiovascular death, while minor reductions in remodeling can be associated with decreased heart failure and cardiovascular death [53].

Reperfusion therapy, fibrinolytic therapy, primary percutaneous coronary intervention and currently available pharmacological treatment such as angiotensin-converting enzyme inhibitors (ACEI), angiotensin receptor blockers (ARB), beta blockers, aldosterone antagonists, to name a few, have been shown to limit, to some extent, cardiac dysfunction and adverse left ventricular (LV) remodeling in patients with acute MI. Current European guidelines support the strategy of starting with ACEI and beta-blockers early after MI [53]. Despite these therapeutic approaches, maladaptive LV remodeling is still observed in a substantial proportion of these patients [39]. Most drugs used to prevent LV remodeling after MI also impair infarct healing and collagen synthesis. Therefore, drugs such as ACEI, ARBs, aldosterone antagonists may prolong the time window of vulnerability for adverse LV remodeling during post-MI healing [53].

Accordingly, new methods and compounds, which can synergistically co-operate with the current available therapies, are still needed to prevent or minimize the time window of vulnerability for adverse cardiac remodeling There is, therefore, a need in the art for compounds and efficient therapeutic methods for the inhibition of maladaptive cardiac remodeling, cardiac rupture and other diseases, conditions, complications and/or disorders associated with heart disease.

Recent studies have shown that TIMP-3 inhibits epidermal growth factor (EGF)/epidermal growth factor receptor (EGFR) signaling via inhibition of MMP activity in the heart [15]. EGF has been implicated in inhibiting collagen synthesis [6, 18, 19] and the expression of TGF-β1 [36] which is a potent inducer of collagen synthesis [3, 20, 21].

Activation of EGFR is known to inhibit collagen synthesis during acute MI, which is critical to infarct scar healing during the early stage of MI. Until now, no method or drug has been designed to target the EGFR function as a treatment of MI.

SUMMARY OF THE INVENTION

The present invention relates to the use of EGF receptor antagonists in methods and compositions for treating heart disease. The present invention relates also to methods and compositions for preventing or minimizing complications associated with heart disease.

As such, in one embodiment, the present invention provides for a pharmaceutical composition for the treatment of heart disease, said composition comprising an EGFR antagonist, and a pharmaceutically acceptable carrier.

In another embodiment, the present invention relates to a pharmaceutical composition for promoting scar healing, the pharmaceutical composition comprising an EGFR antagonist and a pharmaceutically acceptable carrier.

The present invention provides in another embodiment a use of an EGFR antagonist for treating heart disease.

According to another embodiment of the present invention is a use of an EGF receptor antagonist in combination with at least one other heart disease therapy for treating heart disease.

In another embodiment, the present invention provides for a use of an EGFR antagonist for the preparation of a pharmaceutical composition for treatment of heart disease in a subject.

In another embodiment, the present invention relates to a method of treatment of heart disease in a subject comprising administering to the subject an EGF receptor antagonist.

According to another embodiment of the present invention is a method of treatment of a subject for heart disease, the method comprising administering to the subject an EGF receptor antagonist in combination with at least one other heart disease therapy.

In aspects of the invention the at least one other heart disease therapy includes small-molecule drugs, complement inhibitors, beta blockers, angiotensin-converting enzyme inhibitors (ACEI), angiotensin receptor blockers (ARB), aldosterone antagonists, thrombolytic therapy, mechanical cardiac reperfusion or any combinations thereof.

In aspects of the invention heart disease includes acute myocardial infarction, myocardial infarction, heart failure, systolic or diastolic heart failure, heart failure due to hypertension or diabetes, cardiomyopathy, ischemic cardiomyopathy or hypertrophic cardiomyopathy.

In aspects of the invention, the heart disease is myocardial infarction and the EGF receptor antagonist is provided to a subject following myocardial infarction.

In aspects of the present invention, treatment of heart disease includes treating, preventing, minimizing complications associated with heart disease. Complications associated with heart disease include: cardiac hypertrophy, maladaptive myocardial remodeling, long term cardiac remodeling and cardiac rupture.

In aspects of the present invention the subject being treated with the compositions and methods of the present invention is deficient in a tissue inhibitor of matrix metalloproteinase (TIMP). In aspects of the invention the TIMP is TIMP3.

In aspects of the invention the EGFR antagonist is selected in the group consisting of erlotinib, gefitinib, canertinib, PD169540, PD-158780, AG1478, PD153035, CGP59326, PKI166, EKB569, or GW572016.

In aspects of the invention the EGFR antagonist is an EGFR ligand variant capable of inhibiting at least one EGFR-mediated biological activity.

In aspects of the invention the EGFR antagonist is selected from an anti-EGFR antibody, an anti-EGFR antibody fragment, an anti-EGFR ligand antibody or an anti-EGFR ligand antibody fragment.

In aspects of the invention the EGFR antagonist is selected from cetuximab, panitumumab, bevacizumab, zalutumumab, nimotuzumab or matuzumab.

In aspects of the invention the EGFR antagonist is a siRNA, a miRNA, a ribozyme, or an antisense oligonucleotide.

In aspects of the invention the EGFR antagonist is administered by injection.

In aspects of the invention the EGFR antagonist is administered by liposome delivery.

In aspects of the invention the EGFR antagonist is administered via an implantable device capable of sustained release of the EGFR antagonist.

BRIEF DESCRIPTION OF THE DRAWINGS

The invention will be better understood and objects of the invention will become apparent when consideration is given to the following detailed description thereof. Such description makes reference to the annexed drawings wherein.

Panels A and B illustrate collagen I (A) and III (B) expression as measured by real-time PCR. Panel C illustrates collagen I synthesis as measured by N-terminal peptide (PINP) ELISA. Panel D illustrates EGF levels as measured by ELISA. E. TGF-β1 expression as measured by real-time PCR. Data are mean±SEM. N=4-6 mice per group. *P<0.01 vs. corresponding sham within genotype, † P<0.01 vs. WT MI.

Figure 4:
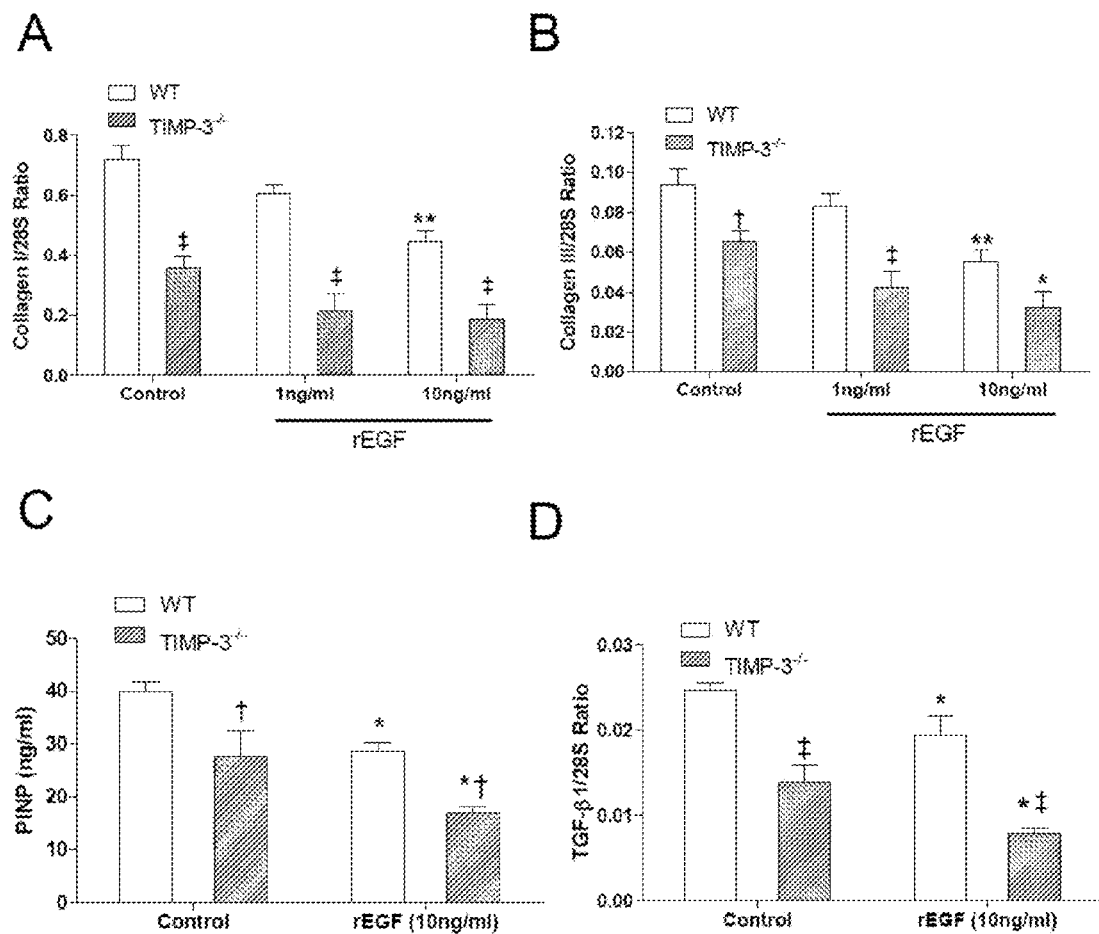

FIG. 4. Panels A, B, C, and D are graphs representing the effect of EGF on collagen synthesis and TGF-β1 expression in adult cardiac myofibroblasts. Panels A and B illustrate the expression of collagen I (A), and III (B) by real-time PCR. Panel C illustrates collagen I synthesis measured by PINP ELISA. Panel D illustrates TGF-β1 expression as measured by real-time PCR. Data are mean±SEM from 5-7 independent experiments. *P<0.05, **P<0.01 vs. corresponding control within genotype; †P<0.05, ‡P<0.01 vs corresponding WT.

Figure 5:
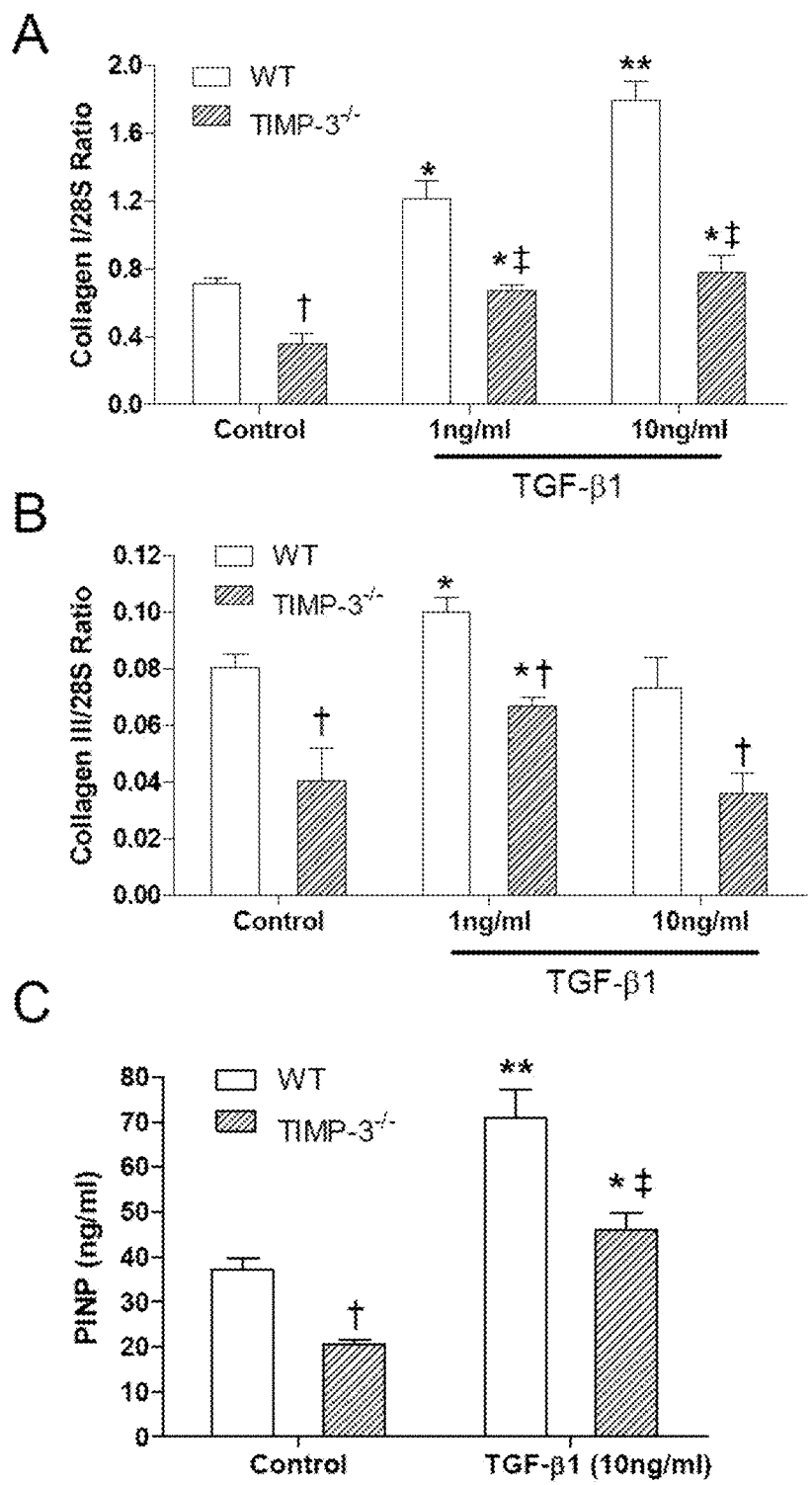

FIG. 5. Panels A, B, and C are graph representing the effect of TGF-β1 on collagen synthesis in adult cardiac myofibroblasts. WT and TIMP-3$^{-/-}$ adult cardiac myofibroblasts subcultured for 2 generations were treated with 1 or 10 ng/ml human recombinant TGF-β1 for 48 hours and mRNA levels of collagen I (A) and III (B) were assessed by real-time PCR analysis, while collagen I synthesis was determined by PINP ELISA (C). Data are mean±SEM from 3-6 independent experiments. *P<0.05, **P<0.01 vs. corresponding control within genotype; †P<0.05, ‡P<0.01 vs corresponding WT.

Figure 6:
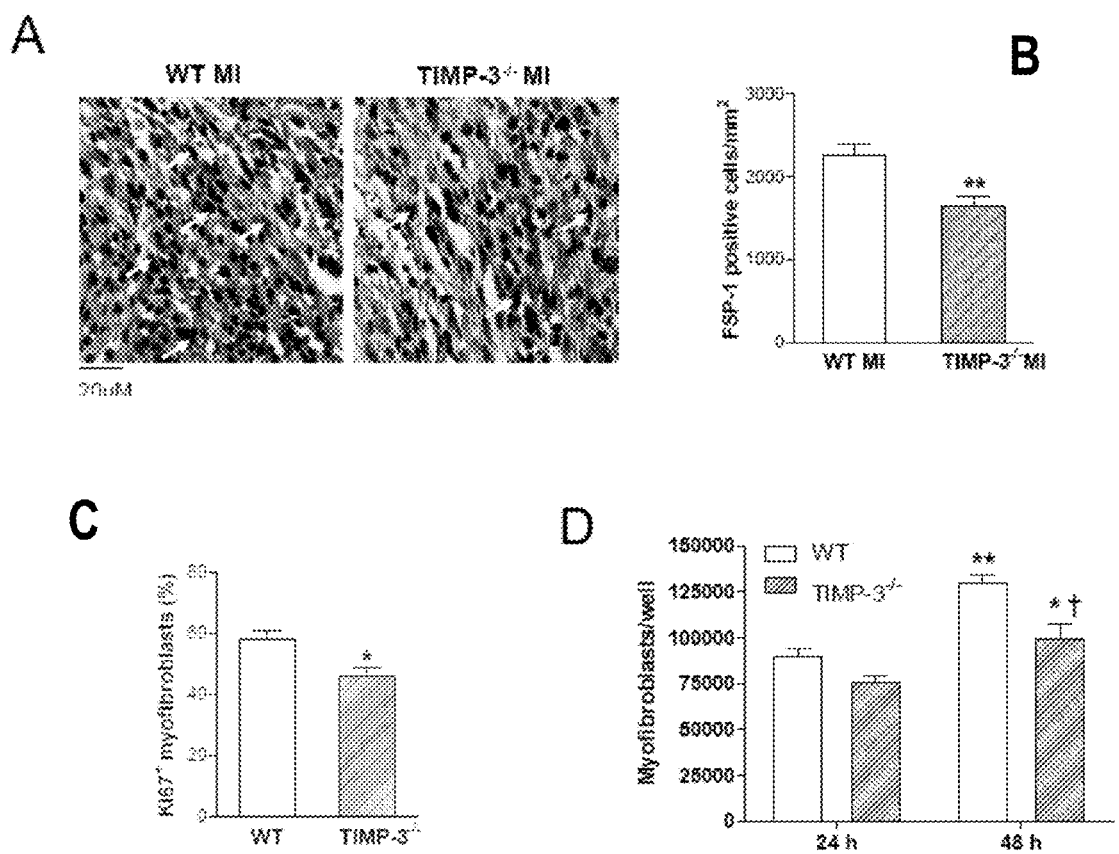

FIG. 6. Panels A, B, C and D are photographs and graphs illustrating and representing adult cardiac myofibroblast proliferation in vivo and in vitro. A. Photographs of (myo)fibroblast proliferation in the infarct myocardium of wild-type (WT) and TIMP-3$^{-/-}$ mice 5 days post-myocardial infarction (MI) measured by FSP-1 staining (white arrows). B. Graph representing the total number of (myo)fibroblasts/mm$^2$ (n=6 per group) in each of photographs of panel A. C. Graph representing percent of Ki67 positive cardiac myofibroblasts cultured from adult WT and TIMP-3$^{-/-}$ mice. D. Graph representing myofibroblast proliferation assessed using the NucleoCounter at 24 and 48 hours post-seeding. Data are mean±SEM. N=4 and 3 independent experiments for C and D, respectively. *P<0.05, ** P<0.01 vs. WT (A and C) or corresponding 24 h within genotype (D); †P<0.01 vs. WT 48 h (D).

DETAILED DESCRIPTION OF THE INVENTION

Definitions

Unless defined otherwise, all technical and scientific terms used herein have the same meaning as commonly understood by one of ordinary skill in the art to which this invention belongs. Also, unless indicated otherwise, except within the claims, the use of "or" includes "and" and vice-versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise.

The term "antisense oligonucleotide" as used herein means a nucleotide sequence that is complimentary to its target.

By "EGFR antagonist" is meant any molecule that inhibits, suppresses or causes the cessation of at least one epidermal growth factor receptor-mediated biological activity, e.g. by reducing, interfering with, blocking, or otherwise preventing the interaction or binding of a native or active EFGR ligand (e.g. EFG) to EGFR.

The term "heart disease" includes acute myocardial infarction, myocardial infarction, heart failure, systolic or diastolic heart failure, heart failure due to hypertension or diabetes, cardiomyopathy, ischemic cardiomyopathy or hypertrophic cardiomyopathy.

By the term "subject" or "subject in need thereof", is intended for a human or non-human mammal affected or likely to be affected with myocardial infarction.

By the term "treating" or "treatment", is meant reversing, minimizing, alleviating, substantially inhibiting the progress of, or preventing the disorder or condition to which such term applies, or one or more symptoms of such disorder or condition.

Therapeutic Methods and Uses

The present invention relates to methods, compositions and uses of epidermal growth factor receptor (EGFR) antagonists in the treatment of heart disease.

As such, one embodiment of the present invention provides for a method of treating heart disease, which may include treating, preventing or minimizing complications associated with heart disease in a subject. The method may include administering to the subject an EGF receptor antagonist. Treatment with the EGFR antagonist may result in inhibiting or substantially inhibiting the EGF receptor signal transduction cascade thereby treating the subject of the heart disease. Complications associated with heart disease that may be treated, prevented or minimized by the methods and compositions of the present invention include: cardiac hypertrophy, maladaptive myocardial remodeling, long term cardiac remodeling and cardiac rupture.

The inventors have, surprisingly, shown that inhibition of EGFR function by an antagonist decreases the incidence of cardiac rupture and improves survival, suggesting that EGFR may be a novel therapeutic target during acute myocardial infraction (MI). The inventors have shown for the first time that an EGFR antagonist may be capable of decreasing the incidence of cardiac rupture and improving post-MI survival.

In one embodiment, inhibition of EGFR function may be used in combination with existing treatments to reduce morbidity and mortality in patients with heart disease, such as acute MI. For example, human studies show that thrombolytic therapy for the treatment of myocardial infarction, although reducing overall patient mortality, may be associated with cardiac rupture, which may be responsible for 6.1% to 12.1% of deaths during the initial 24 to 48 hours following the thrombolytic therapy [1]. Thus, in one embodiment of the present invention provides for a method for treating a subject for heart disease, the method may include administering to the subject an EGF receptor antagonist in combination with at least one other heart disease therapy. The combination of EGFR antagonist and at lease one other heart disease therapy may increase the efficacy of the heart disease therapy. For example, for MI, the subject may also be administered a MI therapy such as small-molecule drugs, complement inhibitors, beta blockers, ACE inhibitors, angiotensin II receptor antagonists (ARBs), aldosterone antagonists, thrombolytic therapy, mechanical cardiac reperfusion or any combinations thereof.

The inventors further discovered that increased incidence in cardiac rupture in post-MI may be due to improper scar healing, i.e. maladaptive remodeling of the heart. Accordingly the present invention may also be directed to a method of treating, preventing or minimizing maladaptive cardiac remodeling. The method may include administering to the subject an effective amount of an EGFR antagonist.

As illustrated in FIG. 4, the inventors discovered that EGF may reduce the synthesis of collagen in cardiac myofibroblasts, and that TGF-B1 stimulates collagen synthesis, as illustrated in FIG. 5. Accordingly, the present invention is also directed to methods of increasing collagen synthesis in myofibroblasts.

EGFR Antagonists

In one embodiment the EGFR antagonists that may be used in the present invention include, EGFR ligand variants. EGFR ligand variants may be polypeptide variants of the epidermal growth factor which may inhibit at least one EGFR-mediated biological activity such as inhibition of the receptor's kinase activation activity. Such polypeptide variants, and nucleic acids encoding these polypeptide variants, may be used to inhibit EGFR activity (see for example U.S. Pat. No. 7,470,769).

In one embodiment, the EGFR antagonist may be a low molecular weight antagonist. Specific examples of low molecular weight EGFR antagonists that may be used in the methods and compositions of the present invention may include erlotinib (Tarceva®) and gefitinib (Iressa®), to name a few. Other EGFR antagonists may include the following EGFR inhibitors: CI-1033 (Canertinib®) (synonyms PD-183805), PD169540, PD-158780, AG1478, PD153035, CGP59326, PKI166, EKB569, or GW572016.

In another embodiment, the antagonist of EGFR may consist of an antibody directed against an EGFR ligand, in such a way that said antibody impairs the binding of the ligand to EGFR. In another embodiment the antagonist of EGFR may consist in an antibody directed against EGFR such as to impair the EGFR-mediated biological activity. Specific examples of antibodies that may be used in the methods and compositions of the present invention include cetuximab (Erbitux®), panitumumab (Vectibix®), bevacizumab (Avastin®), zalutumumab (HuMax-EGFr), nimotuzumab (BIOMab EGFR, Theracim, Theraloc, CIMAher), and matuzumab (formerly EMD 7000), to name a few.

Anti-EGFR antibody (or anti-EGFR-ligand antibody) may be raised according to any known methods by administering an appropriate antigen or epitope to a host animal (e.g., from pigs, cows, horses, rabbits, goats, sheep, and mice, among others). Various adjuvants known in the art may be used to enhance antibody production. Although antibodies useful in practicing the invention may be polyclonal, monoclonal antibodies may be preferred. Monoclonal antibodies against EGFR (or an EGFR ligand) may be prepared and isolated using any technique that provides for the production of antibody molecules by continuous cell lines in culture. Techniques for production and isolation include the hybridoma technique originally described by [40]; the human B-cell hybridoma technique (Cote et al., 1983); and the EBV-hybridoma technique [41]. Alternatively, techniques described for the production of single chain antibodies (see, e.g., U.S. Pat. No. 4,946,778) may be adapted to produce anti-EGFR, or anti-ligand single chain antibodies. EGFR antagonists useful in practicing the present invention also include anti-EGFR, or anti-ligand antibody fragments including but not limited to F(ab') 2 fragments, which can be generated by pepsin digestion of an intact antibody molecule, and Fab fragments, which can be generated by reducing the disulfide bridges of the F(ab') 2 fragments. Alternatively, Fab and/or scFv expression libraries can be constructed to allow rapid identification of fragments having the desired specificity to EGFR or EGFR ligand.

In general, cells actively expressing the protein are cultured or isolated from tissues and the cell extracts isolated. The extracts or recombinant protein extracts, containing the EGFR, are injected in Freund's adjuvant into mice. After being injected 9 times over a three week period, the mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable lines of clones is established which produce the antibody. The monoclonal antibody can then be purified by affinity chromatography using Protein A or Protein G Sepharose.

Cetuximab, an IgG1 chimeric monoclonal antibody, and panitumumab, a fully humanised IgG2 antibody, are epidermal growth-factor receptor (EGFR)-targeted monoclonal antibodies. Both cetuximab and panitumumab are currently used as second-line or third-line chemotherapy for metastatic colorectal cancer.

Additional antibodies targeted to EGFR include: Zalutumumab (HuMax-EGFr), a fully human IgG1 monoclonal antibody (mAb); Nimotuzumab (BIOMAb EGFR, Biocon, India [2]; Theracim, YM Biosciences, Cuba; Theraloc, Oncosciences, Europe, CIMAher, Cuba), a chimeric monoclonal antibody; and Matuzumab (formerly EMD 72000), a humanized monoclonal antibody.

In one embodiment of the invention, the inhibitor of EGFR may be a siRNA, a ribozyme, or an antisense oligonucleotide Antisense oligonucleotides, including anti-sense RNA molecules and anti-sense DNA molecules, that are complimentary to a nucleic acid sequence from an EGFR protein gene may be used in the methods of the present invention to block the translation of EGFR mRNA and inhibit EGFR protein synthesis, or increasing mRNA degradation, thus decreasing the level of EGFR protein, and thus activity, in a cell.

Consequently, the present invention provides a method of inhibiting the effects of EGFR comprising administering an effective amount of an antisense oligonucleotide that is complimentary to a nucleic acid sequence from an EGFR protein gene to an animal in need thereof.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

Small inhibitory RNA (siRNA) is a form of gene silencing triggered by double-stranded RNA (dsRNA). In siRNA sequence-specific, post-transcriptional gene silencing in animals and plants may be initiated by double-stranded RNA (dsRNA) that is homologous in sequence to the silenced gene. A siRNA (small interfering RNA) is designed to target and thus to degrade a desired mRNA (in this case encoding EGFR mRNA) in order not to express the encoded protein (in this case EGFR). Methods relating to the use of siRNA (or RNA interference) to silence genes in C. elegans, Drosophila, plants, and mammals are known in the art [42-52, WO0129058; WO9932619, the disclosures of which are incorporated herein in their entirety].

Ribozymes may also function as inhibitors of EGFR expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GuU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets may also be evaluated by testing their accessibility to hybridization with complementary oligonucleotides, using, e.g., ribonuclease protection assays.

Compositions

In one embodiment, the present invention provides for a composition for treating heart disease, the composition may include an EGFR antagonist, and a pharmaceutically acceptable carrier. In aspects of the present invention, the composition may also be used for treating, preventing or minimizing complications associated with heart disease.

The present inventors have identified novel compositions and methods for inhibiting EGFR signaling. Thus, the present invention provides a means for reducing or inhibiting endogenous EGFR activity thereby minimizing cardiac hypertrophy, maladaptive cardiac remodeling and reducing or inhibiting cardiac rupture or other complications, diseases or disorders associated with heart disease, such as myocardial infarction.

One embodiment of the present invention further encompasses pharmaceutical compositions comprising an EGFR antagonist for administration to subjects in a biologically compatible form suitable for administration in vivo. By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result of eliciting an immune response in a human. A therapeutically effective amount of a substance may vary according to factors such as the disease state/health, age, sex, and weight of the recipient, and the inherent ability of the particular polypeptide, nucleic acid coding therefor, or recombinant virus to elicit a desired immune response. Dosage regimen may be adjusted to provide the optimum therapeutic response. For example, several divided doses may be administered daily or on at periodic intervals, and/or the dose may be proportionally reduced as indicated by the exigencies of the therapeutic situation. The amount of EGFR antagonist for administration will depend on the nature of the EGFR antagonist, the route of administration, time of administration and varied in accordance with individual subject responses. Suitable administration routes may be intramuscular injections, subcutaneous injections, intravenous injections or intraperitoneal injections, oral and intranasal administration. In a preferred embodiment, the administration route may be intravenous injection.

As such, one embodiment of the present invention may be administering the EGFR antagonist by injection. Another embodiment of the present invention may be administering the EGFR antagonist intravenously with a carrier in the form of normal saline solution. Another embodiment of the present invention may be administering the EGFR antagonist by liposome delivery. Another embodiment of the present invention may be administering the EGFR antagonist via an implantable device capable of controlled release of the EGFR antagonist. For example US Pat. Appl. No. 20050208122 (which is incorporated herein by reference) discloses a biodegradable biocompatible implant for controlled release of therapeutically active agents, which may be used to administer the EGFR antagonist according to the embodiments of the present invention.

The compositions described herein may be prepared by per se known methods for the preparation of pharmaceutically acceptable compositions which may be administered to subjects, such that an effective quantity of the active substance (i.e. EGFR antagonist) is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water.

Furthermore the pharmaceutical composition according to the invention may comprise one or more stabilizers such as, for example, carbohydrates including sorbitol, mannitol, starch, sucrose, dextrin and glucose, proteins such as albumin or casein, and buffers like alkaline phosphates.

A major advantage of this invention includes protecting the heart from failure in subjects with heart disease. One advantage of the present invention includes promoting scar healing following myocardial infarction, thereby protecting the heart from heart failure. Promotion of scar healing may be achieved through inhibition of EGFR receptor function and signaling, which is a novel therapeutic target for myocardial infarction. As such, in one embodiment, the present invention is directed to pharmaceutical compositions comprising an EGFR antagonist for promoting scar healing.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

The present study was designed to test the hypotheses that deficiency in TIMP-3 increases cardiac rupture post-MI via epidermal growth factor (EGF)/epidermal growth factor receptor (EGFR) signalling which downregulates TGF-β1 expression and collagen synthesis, and that treatment with cetuximab to inhibit EGFR signaling protects against cardiac rupture post-MI. Using a clinically relevant mouse model of MI, and cellular, molecular techniques, our study showed that incidence of cardiac rupture was increased in TIMP-3$^{-/-}$ mice post-MI via EGF/EGFR signalling which downregulated TGF-β1 expression and collagen synthesis in the infarct myocardium. Treatment with cetuximab decreased cardiac rupture and improved survival in TIMP-3$^{-/-}$ mice post-MI.

Materials and Methods
Animals

Wild-type (WT) mice of the genetic background C57BL/6 were purchased from Charles River Laboratories (Wilmington, Mass.). TIMP3$^{-/-}$ mice were generated as described previously [22] and back-crossed more than 7 generations into the C57BL/6 background. Animals were provided with food and water ad libitum and maintained in a temperature and humidity controlled facility with 12-hour light and dark cycles. A breeding program was carried out to generate adults for this study. Animal studies were approved by the University of Western Ontario Institutional Animal Care and Use Committee, and the investigation conformed with the *Guide for the Care and Use of Laboratory Animals*, published by National Institutes of Health (NIH Publication No. 85-23, revised 1996).

Myocardial Infarction

MI was induced by occlusion of the left anterior descending coronary artery as we have previously described [10]. Experiments were conducted at 5 or 30 days post surgery to mimic early and later stages of heart failure, respectively. Survival was monitored, and incidence of cardiac rupture and the left ventricle to body weight ratio were recorded. Mice with infarct sizes between 30-45% were used in all studies.

Assessment of Cardiac Rupture

Deceased mice were examined within 12 hours. The chest was opened to examine bleeding around the infarct region. Hearts were then removed and the left ventricle (LV) chamber was cannulated with a 20 G blunt end IV catheter via the aorta and perfused with 200 μL saline to determine if there was leakage from the infarct region. Histological examination was conducted to confirm the region of cardiac rupture. Briefly, WT and TIMP-3$^{-/-}$ hearts were isolated after death post-MI and fixed in 4% paraformaldehyde and embedded in paraffin. Samples were then sectioned (5 μm), stained with hematoxylin/eosin and visualized using a Zeiss microscope (Observer D1) as in our previous study [11].

MMP Activity

Matrix metalloproteinase (MMP) activity was measured using the Sensolyte 520 Generic MMP Assay Kit (AnaSpec, CA) as per manufacturer's instructions. Briefly, LV tissues from sham and peri-infarct tissues from MI were collected 2 days after surgery, homogenized and incubated with the FAM/QXL 520 FRET substrate for 1 hour in a black 96-well plate at room temperature in the dark. Measurements were made using a SpectraMax M5 microplate reader at excitation and emission wavelengths of 490 and 520 nm, respectively. A standard curve was created using 5-FAM-Pro-Leu-OH to convert fluorescence values into amount of substrate cleaved. Values are expressed as pmol substrate cleaved/mg protein.

Hydroxyproline Content

LV tissues from sham and infarct regions from MI were isolated 5 days after surgery, dried overnight, weighed the following morning and hydrolyzed. Hydroxyproline concentration was determined using the colorimetric method described by Woessner [34] with modifications. A standard curve was created using L-hydroxyproline to convert sample colorimetric values into mg of hydroxyproline. Values are expressed as mg hydroxyproline/g dry weight.

Measurement of EGF Levels

The LV tissues from sham and infarct regions from MI mice 5 days after surgery were homogenized in phosphate-buffered saline (PBS) and centrifuged. The supernatant was then collected and protein concentrations were measured. EGF protein levels in the LV myocardium were determined using a mouse EGF Quantikine ELISA kit (R&D systems, MN) according to the manufacturer's instructions. Values are expressed as pg EGF levels per mg myocardial tissue.

Stretch Experiments

The left ventricular free wall and infarct region were isolated 5 days after sham or MI surgery. Tissues were cut into 2×5 mm pieces with one end attached to a force transducer and the other end attached to a micromanipulator. Increasing tensions were then applied to the tissue and the force was recorded when rupture occurred. The threshold force to induce scar rupture was adjusted by tissue dimensions measured under a Zeiss dissecting scope.

Isolation and Culturing of Adult Cardiac Myofibroblasts

Cardiac myofibroblast cultures were prepared from ventricles of WT and TIMP-3$^{-/-}$ mice as previously described [14]. Briefly, hearts were aseptically isolated from adult mice. The ventricles were minced and digested with collagenase and disapase. Fibroblasts subcultured for 2 generations were seeded on culture plates and used for all in vitro experiments. After 2 passages virtually all fibroblasts differentiate into myofibroblasts [33]. Purity of myofibroblasts was verified by FSP-1 and α-smooth muscle actin double staining. Cell proliferation was assessed by Ki67 and FSP-1 double staining.

To determine the effect of EGF and TGF-β1 on collagen expression and synthesis, adult cardiac myofibroblasts subcultured for 2 generations were placed in low serum (5% FBS) for 24 hours and subsequently treated with either recombinant mouse EGF (rEGF, R&D Applied Biosystems, CA) in DMEM containing 5% FBS and cultured for another 24 hours or with TGF-β1 (Millipore, Mass.) and cultured for another 48 hours. Cells were then harvested and experiments were conducted.

Myofibroblast Proliferation

In vivo myo(fibroblast) proliferation was determined through fibroblast-specific protein (FSP)-1 immunostaining on heart tissue sections from WT and TIMP-3$^{-/-}$ mice 5 days post-MI. The number of FSP-1 positive cells per mm$^2$ is presented. Counts were conducted by two independent observers.

Collagen I Synthesis

Collagen I synthesis was assessed in the LV myocardium and in conditioned media collected for cultured myofibroblasts using a rat/mouse procollagen I N-terminal peptide (PINP) ELISA kit (IDS-Medicorp, Quebec) according to the manufacturer's instructions. The LV tissues of sham mice and the infarct regions of WT and TIMP-3$^{-/-}$ mice 5 days post-MI were homogenized in PBS and centrifuged. The supernatant was then collected and protein concentrations were measured. For tissues, 25 µg of total protein was used, while for media, 10 µL of conditioned media was used in the assay. Measurements of absorbances were made using SpectraMax M5 microplate reader at a wavelength of 450 nm. Values are expressed as either ng collagen per mg myocardial tissue or ng/ml conditioned media.

Real-Time RT-PCR

Total RNA was extracted from adult cultured myofibroblasts as well as LV tissue of WT and TIMP-3$^{-/-}$ sham and the infarct region of MI mice 5 days post-surgery using Trizol as previously described [26, 27]. cDNA was synthesized using M-MLV reverse transcriptase (Invitrogen, ON). Real-time PCR was conducted using SYBR Green PCR Master Mix as per manufacturer's instructions (Applied Biological Materials, BC). 28S rRNA (house keeping gene) was used as a loading control since previous studies have shown that it is a reliable loading control especially for use in experiments with hypoxia [37] and MI [13].

Hemodynamic Measurements

Cardiac function was measured at 5 and 30 days post-MI using a Millar pressure transducer catheter (Model SPR-839, Size 1.4F) as previously described [24]. Measurements included arterial pressures, heart rate, LV systolic and end-diastolic pressures, as well as the maximal rate of LV pressure development (+dP/dt) and maximal rate of pressure relaxation (−dP/dt). Animals were sacrificed after hemodynamic measurements and cardiac hypertrophy was assessed by determination of the heart weight (mg) to the body weight (g) ratio.

Cetuximab Treatment

Following MI, WT and TIMP-3$^{-/-}$ mice were treated with cetuximab (Erbitux®, 10 mg/kg) immediately by an IV injection, which was followed by IP injections at day 3 and 5 post-MI, respectively. Survival was monitored for 30 days after MI. Hemodynamic measurements were made at 5 and 30 days post-MI. Post-mortem examinations were performed in all mice that died after MI to identify cardiac ruptures.

Statistical Analysis

Data are presented as mean±SEM. Unpaired Student's t test, Chi-square, one- or two-way ANOVA followed by Bonferroni post tests were performed as appropriate. P<0.05 was considered statistically significant.

Results

Survival and Cardiac Function Post MI

WT (n=74) and TIMP-3$^{-/-}$ (n=81) mice were subjected to MI or sham operations, and survival was followed up to 30 days after surgery. MI resulted in a significant decrease in survival in both WT and TIMP-3$^{-/-}$ mice compared to the sham operated groups (P<0.05, FIG. 1A). Furthermore, following MI, survival was significantly decreased in TIMP-3$^{-/-}$ mice as compared to WT (P<0.001, FIG. 1A). There was no significant difference in infarct size between WT and TIMP-3$^{-/-}$ mice at 5 days (38.6±2.9% vs. 38.3±3.3%) or 30 days (37.9±2.0% vs. 41.3±3.3%) post-MI. To determine if the decrease in survival observed in the TIMP-3$^{-/-}$ mice following MI was due to cardiac dysfunction, hemodynamic analysis was performed at 5 and 30 days post-MI. To that end, we measured heart rate (HR), mean arterial pressure (MAP), left ventricular systolic pressure (LVSP), left ventricular end diastolic pressure (LVEDP), and maximal positive and minimal negative first derivative of left ventricular pressure (+dP/dt$_{max}$ and −dP/dt$_{min}$) using the Millar tip-transducer catheter. Our data demonstrated that there were no significant differences in any of the parameters after sham or MI surgery between WT and TIMP-3$^{-/-}$ mice (P=n.s., Table 1). Furthermore, there was no significant difference in cardiac hypertrophy as measured by heart/body weight ratio between WT and TIMP-3$^{-/-}$ (3.6±0.19 vs. 3.4±0.21 mg/g, P=n.s.) mice at 30 days post-MI. Taken together these data suggest that the increased mortality in the TIMP-3$^{-/-}$ is not due to cardiac dysfunction.

Cardiac Rupture Post-MI

Figure 1:
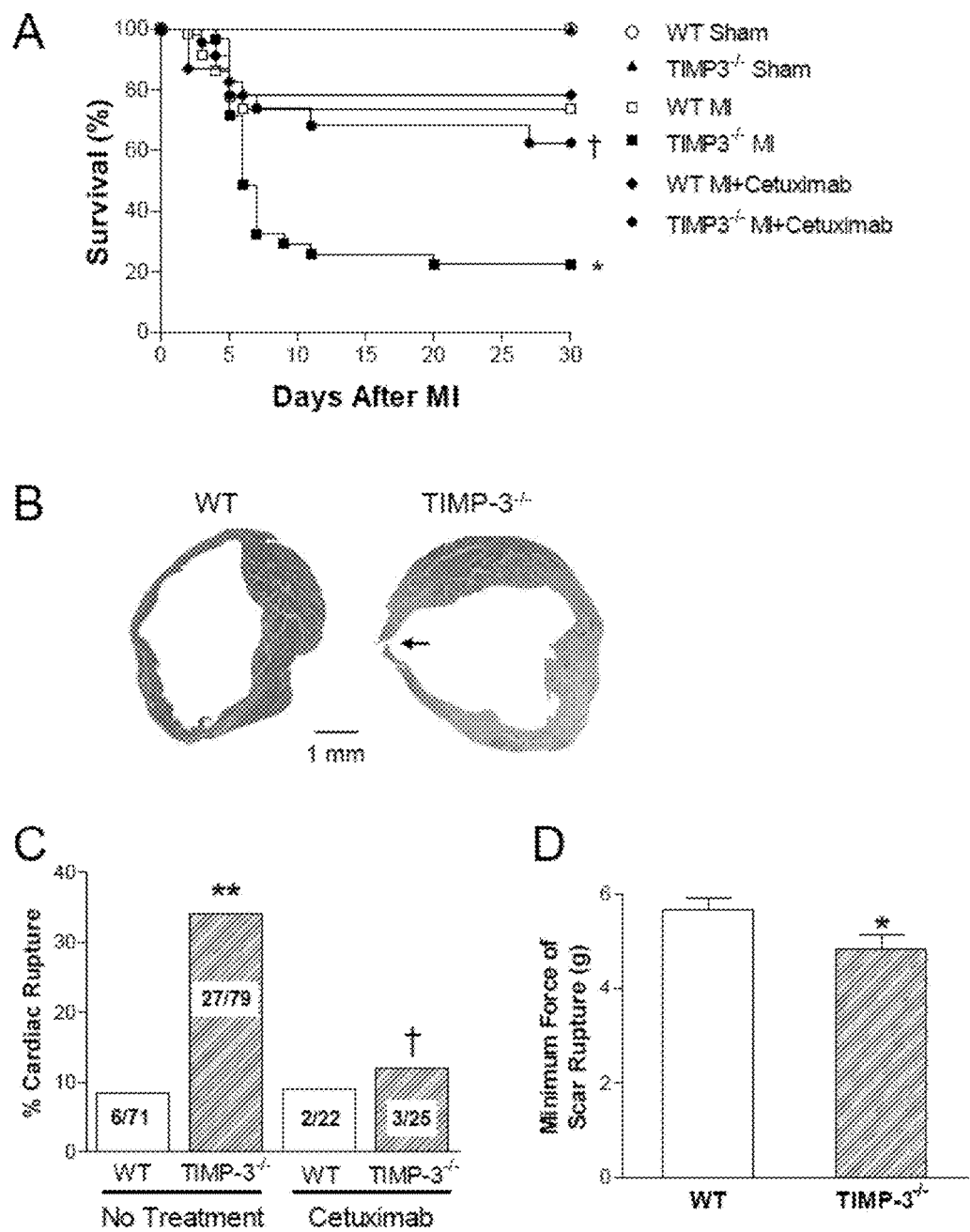
FIG. 1 includes graphs (panels A, C and D) are and a photograph (panel B) representing survival and cardiac rupture after myocardial infarction (MI) in wild-type (WT) and TIMP-3$^{-/-}$ mice. A. Illustrated are Kaplan-Meier survival curves of WT and TIMP-3$^{-/-}$ mice after MI with and without treatment with the EGFR antagonist cetuximab. Thirty-day survival and MI was significantly decreased in TIMP-3$^{-/-}$ compared to WT mice post-MI (* $P<0.001$), which was rescued by cetuximab treatment († $P<0.01$). B. Illustrated is a photograph of a typical example of left ventricular (LV) wall of a WT mice and the LV of a TIMP-3$^{-/-}$ wall showing cardiac rupture (arrow) (hemotoxylin and eosin staining) C. Graph showing incidence of cardiac rupture after MI with and without cetuximab treatment. Numbers in bars are rupture/total mouse numbers. D. Graph illustrating determination of the force required to induce infarct scar rupture. The infarct scar was isolated 5 days post-MI and used for the stretch experiment (n=10-11 per group). Error bars are ±SEM; *$P<0.05$, **$P<0.001$ vs. WT.

To determine a possible cause for the increase in mortality in TIMP-3$^{-/-}$ mice following MI, a post-mortem was performed. LV free wall cardiac rupture as confirmed by histological examination in addition to evidence of bleeding and perfusion leakage from the infarct region was found in both groups. A typical example of infarct rupture is shown in FIG. 1B (arrow). TIMP-3 deficiency resulted in a 4-fold increase in the incidence of cardiac rupture following MI as compared to WT mice (P<0.001, FIG. 1C). Stretch experiments were conducted to determine the force required to induce infarct scar rupture. Our results demonstrated that the force required to induce scar rupture in the TIMP-3$^{-/-}$ mice following MI was significantly lower than that for WT (P<0.05, FIG. 1D). There was no significant difference in the force inducing rupture between WT and TIMP-3$^{-/-}$ mice (15.7±1.9 vs. 16.4±2.5 grams, P=n.s.) following sham operations.

Effects of Cetuximab on Cardiac Rupture, Function and Survival

Treatment with cetuximab (10 mg/kg) immediately, and at day 3 and 5 post-MI significantly decreased the incidence of cardiac rupture in TIMP-3$^{-/-}$ mice (12% vs. 34%, P<0.05, FIG. 1C). Although cardiac function was not significantly different at day 5, LVSP and LV+dP/dt were significantly increased after cetuximab treatment in TIMP-3$^{-/-}$ mice 30 days post-MI (P<0.05, Table 1), indicating significant improvement in contractile function. Furthermore, treatment with cetuximab significantly improved 30-day survival post-MI in TIMP-3$^{-/-}$ mice (62.5% vs. 22.7%, P<0.01, FIG. 1A). However, cetuximab treatment did not have any significant effect on cardiac rupture, function or survival in WT mice (P=n.s., Table 1, FIGS. 1A and C).

ECM Remodeling, EGF and TGF-β1 Expression Post-MI

Figure 2:
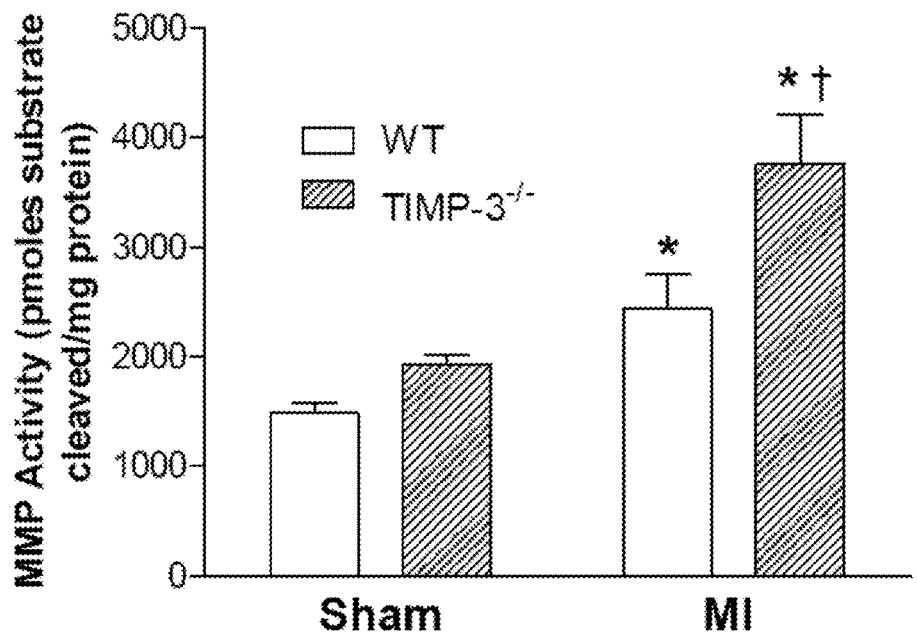
FIG. 2. Panels A, and B are graphs representing assessment of MMP activity and collagen content in wild-type (WT) and TIMP-3$^{-/-}$ mice. A. MMP activity was assessed in the peri-infarct zone 2 days post-MI using a fluorescence based assay. B. Collagen content was assessed 5 days post-MI in the infarct region by hydroxyproline measurement. Data are mean±SEM. N=4-6 mice per group. *$P<0.01$ vs. corresponding sham within genotype, † $P<0.01$ vs. WT MI.
Figure 2:
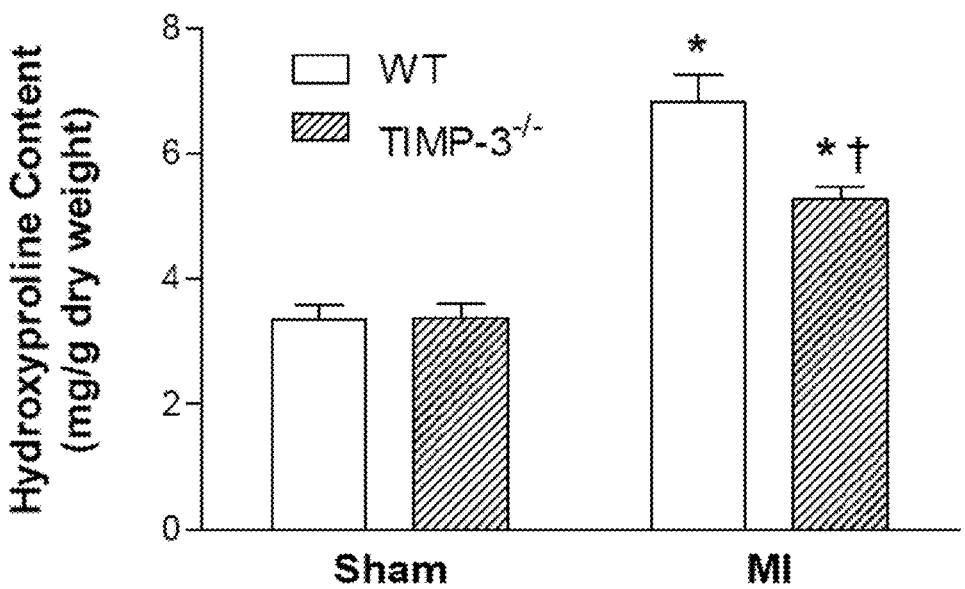
Figure 3:
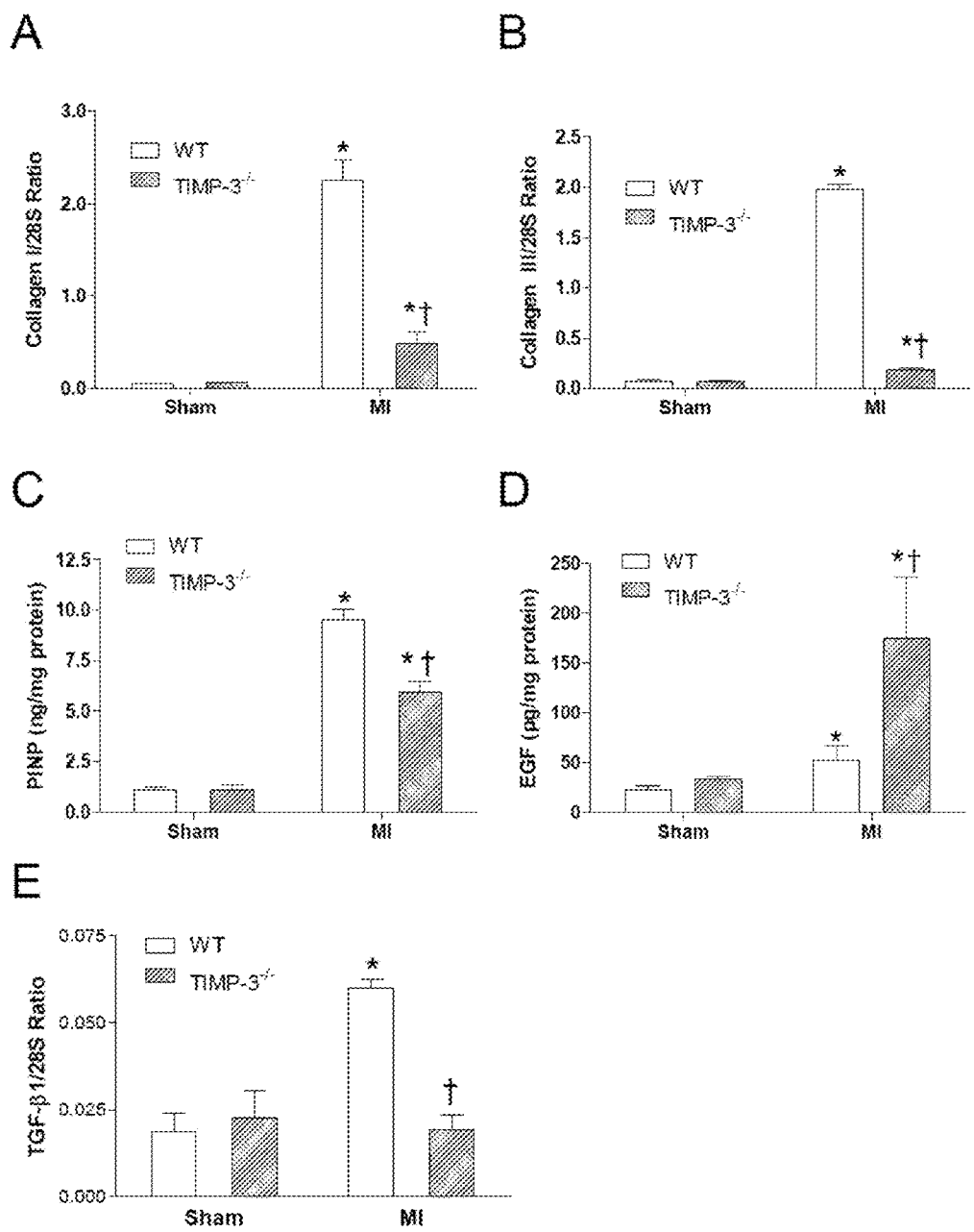
FIG. 3. Panels A, B, C, D and E are graphs representing collagen levels, EGF and TGF-β1 expression in sham LV tissues and in the infarct region after myocardial infarction (MI) in wild-type (WT) and TIMP-3$^{-/-}$ mice 5 days post-MI.

To determine a potential mechanism for cardiac rupture in the TIMP-3$^{-/-}$ mice, we measured MMP activity and collagen content. MMP activity was measured at 2 days post-MI since previous studies have shown that MMP activity is elevated shortly post-MI [9]. Collagen content was assessed at 5 days post-MI, a time point at which mortality was the highest as demonstrated by the survival curve (FIG. 1A). Our results showed that MMP activity was significantly increased in WT and TIMP-3$^{-/-}$ mice post-MI as compared to sham controls. Moreover, MMP activity was significantly higher in TIMP-3$^{-/-}$ mice compared to their WT counterparts post-MI (P<0.01, FIG. 2A). The collagen content, as determined by hydroxyproline measurement was significantly increased in both WT and TIMP-3$^{-/-}$ mice following MI as compared to their respective shams. However, TIMP-3$^{-/-}$ mice had significantly lower levels of collagen in the infarct region compared to WT following MI (P<0.01, FIG. 2B). Furthermore, determination of the collagen expression through real-time PCR analysis revealed that collagen I and III mRNA levels in the infarct myocardium were increased in WT and TIMP-3$^{-/-}$ mice as compared to sham controls. However, the TIMP-3$^{-/-}$ mice had significantly lower collagen expression levels compared to their WT counterparts following MI (P<0.01, FIGS. 3A and 3B). In addition, since collagen I is the predominant collagen isoform in the heart, [3, 9] we measured its synthesis using an ELISA kit that assesses collagen I N-terminal propeptide (PINP) levels. Our data showed that collagen I synthesis was significantly elevated in both WT and TIMP-3$^{-/-}$ mice following MI as compared to their respective shams, however there was significantly lower collagen I synthesis in the TIMP-3$^{-/-}$ as compared to WT mice post-MI (P<0.01, FIG. 3C).

As EGF inhibits collagen synthesis [18, 19] and regulates the expression of TGF-β1 [36], a critical inducer for collagen production [3, 20, 21] and since we have recently demonstrated that TIMP-3 inhibits EGF signaling in the heart [15], we measured EGF and TGF-β1 levels in both WT and TIMP-3$^{-/-}$ mice following MI. Our results showed that EGF levels were significantly increased (P<0.05, FIG. 3D) while TGF-β1 levels were significantly decreased in the infarct myocardium of TIMP-3$^{-/-}$ mice as compared to WT (P<0.01, FIG. 3E). These data suggest that TIMP-3 inhibits EGF but promotes TGF-β1 expression. Furthermore, EGF levels were negatively correlated with collagen and TGF-β1 expression (FIGS. 3A-E).

Effect of EGF on Collagen Synthesis and TGF-β1 Expression in Adult Cardiac Myofibroblasts To further demonstrate a negative effect of EGF on collagen and TGF-β1 expression, adult cardiac myofibroblasts were cultured, as these cells produce the majority of the collagen in the heart [3]. Treatment of adult cardiac myofibroblasts with 1 ng/ml EGF (low concentration) had little effect on collagen I or III expression. However, treatment with 10 ng/ml EGF (high concentration) resulted in a significant decrease in collagen I and III expression (P<0.01, FIGS. 4A and 4B), a decrease in collagen I synthesis (P<0.01, FIG. 4C) as well as a decrease in TGF-β1 expression (P<0.01, FIG. 4D) in both WT and TIMP-3$^{-/-}$ myofibroblasts. The decrease was more pronounced in the TIMP-3$^{-/-}$ as compared to WT for collagen I (47% vs 38%), and collagen III (51% vs 41%) expression, collagen I synthesis (39% vs 28%) and TGF-β1 (43% vs 22%) levels, respectively (P<0.01, FIGS. 4A-D). These data showed that EGF inhibits collagen I and III as well as TGF-β1 expression in the cardiac myofibroblasts.

Effects of TGF-β1 on Collagen Synthesis in Adult Cardiac Myofibroblasts

To demonstrate a causal relationship between TGF-β1 and collagen synthesis, cultured adult cardiac myofibroblasts from WT and TIMP-3$^{-/-}$ mice were employed. Treatment of adult cardiac myofibroblasts with 1 ng/ml TGF-β1 (low concentration) resulted in a significant increase in collagen I and III expression (P<0.05, FIGS. 5A and B). Treatment with 10 ng/ml TGF-β1 (high concentration) resulted in a further increase in collagen I expression and synthesis (P<0.01, FIGS. 5A and C) while it had no effect on collagen III compared to controls (P=n.s., FIG. 5B). These effects of TGF-β1 were significantly decreased in TIMP-3$^{-/-}$ compared to WT myofibroblasts (P<0.01, FIGS. 5A-C).

These results demonstrated that TGF-β1 promotes collagen synthesis in the cardiac myofibroblasts.

TIMP-3 Deficiency Decreases Adult Cardiac Myofibroblast Proliferation

As previous studies have shown that overexpression of TIMP-3 using an adenoviral construct increases cardiac fibroblast proliferation [23], we wanted to determine whether the decrease in collagen synthesis in the TIMP-3$^{-/-}$ may be due to, at least in part, a decrease in (myo)fibroblast proliferation. To that end, the LV tissue sections of WT and TIMP-3$^{-/-}$ mice at 5 days post-MI were subjected to immunostaining using the fibroblast specific protein-1 (FSP-1) (FIG. 6A), which is expressed in the nucleus and the cytoplasm of fibroblasts and myofibroblasts [25]. Our data showed that the number of (myo)fibroblasts was significantly decreased in the infarct region of TIMP-3$^{-/-}$ mice as compared to their WT counterparts after MI (P<0.01, FIG. 6B). To further study the role of TIMP-3 in cardiac myofibroblast proliferation, adult cardiac myofibroblasts were isolated and cultured for 2 generations. The culture was determined to be 99% pure through immunostaining of FSP-1 (not shown). We also stained for α-smooth muscle actin (not shown), a marker which is expressed in myofibroblasts but not fibroblasts. Our results showed that virtually all cells at passage 2 were myofibroblasts as confirmed by α-smooth muscle actin and FSP-1 double staining. This is consistent with a previous finding that the majority of the fibroblasts in culture differentiate into myofibroblasts by the second passage [33]. Proliferation of the myofibroblasts was assessed by Ki67 and FSP-1 double staining (not shown) and confirmed using the NucleoCounter at 24 and 48 hours post seeding (FIG. 6D). Our data showed that loss of TIMP-3 resulted in a significant decrease in cardiac myofibroblast proliferation (FIGS. 6C and 6D).

Discussion

Cardiac rupture is a fatal complication after MI, however its underlying molecular mechanisms are not fully understood [30]. The present study demonstrated that TIMP-3 deficiency results in a significant increase in mortality and incidence of cardiac rupture post-MI. Furthermore, TIMP-3 deficiency increased EGF levels, decreased myofibroblast proliferation, decreased TGF-β1 and collagen synthesis and therefore, decreased overall collagen content in the infarct myocardium. Importantly, we showed for the first time that treatment with cetuximab decreased incidence of cardiac rupture, improved cardiac function and survival in TIMP-3$^{-/-}$ mice post-MI.

TIMP-3 has been shown to play an important physiological role within the heart as its absence triggers progressive myocardial remodeling and dysfunction with characteristic matrix degradation, cytokine activation and myocardial apoptosis similar to human heart failure in aged mice (21-23 months old) even without imposed stresses [7, 8]. Our data showed that mortality was significantly increased in TIMP-3$^{-/-}$ mice following MI as compared to WT. The majority of the observed mortality in TIMP-3$^{-/-}$ mice occurred around day 5 post-MI. To determine whether cardiac dysfunction could contribute to the increase in mortality observed in TIMP-3$^{-/-}$ mice, we performed hemodynamic analysis on WT and TIMP-3$^{-/-}$ mice following sham or MI operations. Importantly, all the mice used in our study were between 2-6 months of age to minimize influences of aging in the present study. Our data demonstrated that there were no significant differences in cardiac function between WT and TIMP-3$^{-/-}$ at 5 or 30 days post-MI. Furthermore, there was no significant difference in cardiac hypertrophy between WT and TIMP-3$^{-/-}$ at 30 days post-MI. Therefore, unlike the study by Tian et al. [32], our results suggest that the increased mortality in the TIMP-3$^{-/-}$ is not due to cardiac dysfunction. This discrepancy between our study and that conducted by Tian et al. is not completely clear, but could be due to differences in the severity of the MI model. The infarct sizes used in our study were between 30-45%, whereas Tian et al. [32] did not measure infarct size in their study. In our study there was approximately a 50% decrease in survival in the TIMP-3$^{-/-}$ mice as compared to WT, whereas in their study the decrease was only 20%, suggesting that our model was much more severe. A severe model of MI would therefore cause a significant decrease in cardiac function in both groups, thus making it difficult to see differences between WT and TIMP-3$^{-/-}$ mice.

To determine a possible cause for the increased incidence of mortality in the TIMP-3$^{-/-}$ mice following MI, a post-mortem was performed and cardiac rupture as confirmed by histological examination was found to be the primary cause of death. Stretch experiments were then conducted to investigate if TIMP-3$^{-/-}$ mice had weakened scar tissues. Our results demonstrated that the force required to induce scar rupture in the TIMP-3$^{-/-}$ mice following MI was significantly lower than that for WT. These data suggest that there is improper scar healing in the TIMP-3$^{-/-}$ mice. To further study potential mechanisms responsible for the weakened scar tissue in TIMP-3$^{-/-}$ mice, MMP activity and collagen content were measured. We demonstrated that MMP activity was significantly elevated in the TIMP-3$^{-/-}$ mice, and the collagen content was significantly reduced. These results are in agreement with a previous study that showed reduced collagen content and increased MMP activity in the TIMP-3$^{-/-}$ myocardium following MI [32]. Furthermore, determination of the collagen expression revealed that collagen I and III were increased in WT and TIMP-3$^{-/-}$ mice following MI as compared to sham controls. A novel finding in our study is that the TIMP-3$^{-/-}$ mice had significantly lower collagen expression and synthesis levels compared to their WT counterparts following MI. Thus, the decrease in collagen content assessed through measurement of hydroxyproline content is not only due to increased matrix degradation as was previously thought, but also due to decreased collagen synthesis.

We recently demonstrated that TIMP-3 inhibits EGF/EGFR signaling in the heart [15]. EGF has been shown to regulate the expression of TGF-β1, a major inducer of collagen in several cell types [5, 36]. However, the effects of EGF on TGF-β1 expression and collagen synthesis in the heart have not been previously investigated. We therefore measured EGF and TGF-β1 levels in the infarct myocardium. Our results demonstrated that myocardial EGF levels were significantly elevated, while those of TGF-β1 were significantly reduced in TIMP-3$^{-/-}$ mice following MI as compared to WT. To further study the effects of EGF and TGF-β1 on collagen expression, adult cardiac myofibroblasts were cultured and treated with recombinant EGF or TGF-β1. Our data demonstrated that treatment with recombinant EGF significantly inhibited collagen synthesis and TGF-β1 expression in cardiac myofibroblasts and the opposite effect on collagen synthesis was observed following TGF-β1 treatment.

TIMP-3 has been shown to promote myofibroblast proliferation [23, 35] which are the main producers of collagen in the heart [3]. In the present study, we wanted to determine whether the decrease in collagen synthesis could be explained, at least in part, by a decrease in myofibroblast proliferation in TIMP-3$^{-/-}$ mice. Our results demonstrated that there was a significant decrease in the number of myofibroblasts in the TIMP-3$^{-/-}$ compared to WT mice post-MI. Furthermore, a decrease in proliferation was also verified in primary cultures of adult cardiac myofibroblasts from TIMP-3$^{-/-}$ mice. Taken together, our data suggest that deficiency in TIMP-3 decreases cardiac myofibroblast proliferation and collagen synthesis via EGFR signalling in the infarct myocardium.

To further study the role of EGFR signalling in infarct healing post-MI, we employed cetuximab, a chimeric monoclonal antibody against EGFR. Treatment with cetuximab decreased the incidence of cardiac rupture, and significantly improved cardiac function and survival in TIMP-3$^{-/-}$ mice post-MI. These data suggest a key role of EGFR signalling responsible for cardiac rupture and high mortality in TIMP-3$^{-/-}$ mice post-MI. It should be noted that cetuximab did not have any effects on cardiac rupture, function and survival in the WT mice. The reason for this is not completely clear. Activities of TIMP-3 and MMPs are critical to ECM remodeling and infarct scar healing. In the WT, the activities of TIMP-3 and MMPs appear to be balanced as evidenced by the low incidence of cardiac rupture post-MI. In addition, TIMP-3 inhibits MMP activity and decreases EGF ligand shedding as shown by a significantly lower EGF levels in WT compared to TIMP-3$^{-/-}$ mice post-MI. Furthermore, our in vitro studies showed that treatment of cardiac myofibroblasts with a low dose of EGF had little effect on collagen expression, only a high dose of EGF caused a significant decrease in TGF-β1 expression and collagen I synthesis. These data suggest that EGF/EGFR activity may be much lower in WT in comparison to TIMP-3$^{-/-}$ mice. Thus, treatment with cetuximab appears to have had no effects in the WT mice. Since the incidence of cardiac rupture in the C57BL/6 WT mice is so low, it may be difficult to show the effects of cetuximab in these animals. Interestingly, studies have shown that the incidence of cardiac rupture in 129sv mice is more than double in C57BL/6 mice post-MI [57]. The 129sv mice would therefore represent an interesting model to study the effects of cetuximab in future investigations.

In conclusion, the present study demonstrated deficiency in TIMP-3 increases cardiac rupture post-MI via EGF/EGFR signalling and downregulation of TGF-β1 expression and collagen synthesis in the infarct myocardium. Inhibition of EGFR by cetuximab protects against cardiac rupture and improves survival in TIMP-3$^{-/-}$ mice post-MI. Our study suggests that cetuximab may have therapeutic potential in protecting against cardiac rupture after MI, especially in patients with thrombolytic therapy where risk of cardiac rupture is much higher [1].

TABLE 1

Hemodynamic changes in wild type (WT) and TIMP-3−/− mice following myocardial infarction (MI) with and without cetuximab (Cetux) treatment.

| | WT | | | TIMP-3−/− | | |
|---|---|---|---|---|---|---|
| | Sham | MI | MI + Cetux | Sham | MI | MI + Cetux |
| 5 days post-MI | | | | | | |
| | n = 9 | n = 9 | n = 5 | n = 8 | n = 6 | n = 5 |
| Heart Rate (bpm) | 369 ± 13 | 427 ± 20 | 429 ± 35 | 401 ± 23 | 390 ± 28 | 412 ± 14 |
| MAP (mmHg) | 85.6 ± 6.0 | 72.4 ± 5.0* | 62.1 ± 4.5* | 93.8 ± 7.2 | 69.3 ± 9.8* | 67.0 ± 4.5* |
| LVSP (mmHg) | 110.4 ± 5.7 | 86.6 ± 3.6* | 76.5 ± 4.9* | 104.7 ± 9.7 | 84.3 ± 8.0* | 72.5 ± 3.9* |
| LVEDP (mmHg) | 5.1 ± 0.9 | 8.2 ± 1.1 | 9.8 ± 2.5 | 5.3 ± 0.8 | 6.3 ± 1.2 | 7.1 ± 0.9 |
| LV +dP/dt (mmHg s$^{-1}$) | 6257 ± 538 | 4593 ± 365* | 4428 ± 676* | 5911 ± 542 | 4988 ± 745* | 4981 ± 885* |
| LV −dP/dt (mmHg s$^{-1}$) | 6021 ± 458 | 4501 ± 367* | 3974 ± 455* | 5760 ± 433 | 4468 ± 587* | 4206 ± 568* |
| 30 days post-MI | | | | | | |
| | n = 8 | n = 13 | n = 7 | n = 8 | n = 7 | n = 7 |
| Heart Rate (bpm) | 435 ± 21 | 421 ± 11 | 381 ± 17 | 434 ± 11 | 396 ± 19 | 371 ± 17 |
| MAP (mmHg) | 99.0 ± 7.5 | 77.0 ± 4.2* | 74.9 ± 3.7 | 98.4 ± 5.9 | 65.0 ± 5.8* | 79.9 ± 4.2* |
| LVSP (mmHg) | 114.2 ± 6.0 | 93.5 ± 3.1* | 94.3 ± 7.0 | 112.4 ± 6.9 | 87.1 ± 6.0* | 117.7 ± 11.8† |
| LVEDP (mmHg) | 5.9 ± 1.6 | 9.2 ± 1.0 | 11.5 ± 2.6 | 4.4 ± 0.2 | 7.0 ± 1.2 | 9.0 ± 2.8 |
| LV +dP/dt (mmHg s$^{-1}$) | 9106 ± 722 | 5572 ± 305* | 5523 ± 376 | 9155 ± 722 | 5422 ± 571* | 7312 ± 463*† |
| LV −dP/dt (mmHg s$^{-1}$) | 8833 ± 702 | 5295 ± 284* | 5767 ± 391 | 9184 ± 907 | 5328 ± 595* | 6996 ± 931 |

Abbreviations: MAP, mean arterial pressure; LVSP, left ventricular systolic pressure; LVEDP, left ventricular end diastolic pressure;
Data are mean ± SEM,
*$P < 0.05$ vs. sham within genotype.
†$P < 0.05$ vs. MI in TIMP-3−/− mice.

Example 2

As previously stated, most of the commonly drugs used to prevent left ventricular remodeling after MI (i.e. ACEI, ARB, aldosterone antagonists) impair healing and collagen synthesis. Accordingly, these drugs tend to prolong the time window of vulnerability for adverse cardiac remodeling during post-MI healing [53]. Accordingly, a new method for optimizing healing of the heart is needed.

It is proposed that cetuximab and other EGFR antagonists will have an added benefit in wild-type mice treated with an ACE inhibitor post-MI. As the incidence of cardiac rupture is low in WT mice, the combination of cetuximab and ACE inhibitor will show the beneficial effects of cetuximab on cardiac remodeling. Similar results are expected for the combination of cetuximab with beta blockers, angiotensin receptor antagonists (ARBs), and aldosterone antagonists, all of which are known to have beneficial effects on cardiac remodeling.

Adult male C57BL6 mice will be randomly assigned to cetuximab (10 mg/kg, iv, twice a week), enalapril (10 mg/kg/day, po), or cetuximab plus enalapril treatment groups (n=30 mice per group). Mice will be subjected to ligation of the left descending coronary artery to induce MI. Immediately after coronary artery ligation, mice will be treated with either cetuximab, enalapril or combination of cetuximab and enalapril for 30 days. Survival will be monitored for 30 days after MI. Hemodynamic measurements will be made at 5 and 30 days post-MI. To identify cardiac rupture, postmortem examinations will be performed in all mice died after MI. TGFβ expression, MMP activity and collagen synthesis in the infarct myocardium will be also determined. To assess cardiac remodeling, infarct size, LV chamber size, hypertrophy of non-infarct myocardium and cardiomyocyte cell size will be determined.

Similar experiments will be carried out with other EGFR antagonists.

It is expected that combination of the EGFR antagonist (i.e. cetuximab) and enalapril treatment will significantly decrease maladaptive cardiac remodeling, and improve cardiac function and survival post-MI compared to cetuximab or enalapril monotherapies.

Example 3

Interestingly, the 129sv mice have been shown to have a significantly higher incidence of cardiac rupture compared to C57BL/6 mice after MI (56, 57). The 129sv mice therefore represent an excellent model to study the effects of cetuximab on cardiac rupture induced by MI.

Adult male 129sv mice will be randomly assigned to vehicle control and cetuximab (10 mg/kg, iv) treatment groups (n=50 mice per group). Mice will be subjected to ligation of the left descending coronary artery to induce MI.

Immediately after coronary artery ligation, mice will be treated with either vehicle or cetuximab (10 mg/kg, iv). This will be followed by IV injections at day 3 and 5 post-MI, respectively. Survival will be monitored for 30 days after MI. Hemodynamic measurements will be made at 5 and 30 days post-MI. To identify cardiac rupture, postmortem examinations will be performed in all mice died after MI. TGFβ expression, MMP activity and collagen synthesis in the infarct myocardium will also be determined.

Similar experiments will be carried out with EGFR antagonists other than cetuximab.

It is expected that EGFR antagonist treatment will significantly decrease the incidence of cardiac rupture, improve survival and cardiac function in 129sv mice post-MI.

The above disclosure generally describes the present invention. Changes in form and substitution of equivalents are contemplated as circumstances may suggest or render expedient. Although specific terms have been employed herein, such terms are intended in a descriptive sense and not for purposes of limitation. Other variations and modifications of the invention are possible. As such modifications or variations are believed to be within the sphere and scope of the invention as defined by the claims appended hereto.

NON-PATENT REFERENCES

1. Becker R C, Gore J M, Lambrew C, Weaver W D, Rubison R M, French W J, Tiefenbrunn A J, Bowlby L J, Rogers W J (1996) A composite view of cardiac rupture in the United States National Registry of Myocardial Infarction. J Am Coll Cardiol 27:1321-1326
2. Brew K, Dinakarpandian D, Nagase H (2000) Tissue inhibitors of metalloproteinases: evolution, structure and function. Biochim Biophys Acta 1477:267-283
3. Brown R D, Ambler S K, Mitchell M D, Long C S (2005) The cardiac fibroblast: therapeutic target in myocardial remodeling and failure Annu Rev Pharmacol Toxicol 45:657-687
4. Cleutjens J P, Verluyten M J, Smiths J F, Daemen M J (1995) Collagen remodeling after myocardial infarction in the rat heart. Am J Pathol 147:325-338
5. Cosgaya J M, Aranda A (1996) Ras- and Raf-mediated regulation of transforming growth factor beta 1 gene expression by ligands of tyrosine kinase receptors in PC12 cells. Oncogene 12:2651-2660
6. Creely J J, DiMari S J, Howe A M, Hyde C P, Haralson M A (1990) Effects of epidermal growth factor on collagen synthesis by an epithelioid cell line derived from normal rat kidney. Am J Pathol 136:1247-1257
7. Fedak P W, Altamentova S M, Weisel R D, Nili N, Ohno N, Verma S, Lee T Y, Kiani C, Mickle D A, Strauss B H, Li R K (2003) Matrix remodeling in experimental and human heart failure: a possible regulatory role for TIMP-3. Am J Physiol Heart Circ Physiol 284:H626-H634
8. Fedak P W, Smookler D S, Kassiri Z, Ohno N, Leco K J, Verma S, Mickle D A, Watson K L, Hojilla C V, Cruz W, Weisel R D, Li R K, Khokha R (2004) TIMP-3 deficiency leads to dilated cardiomyopathy. Circulation 110:2401-2409
9. Fedak P W, Verma S, Weisel R D, Li R K (2005) Cardiac remodeling and failure From molecules to man (Part II). Cardiovasc Pathol 14:49-60
10. Feng Q, Lu X, Jones D L, Shen J, Arnold J M (2001) Increased inducible nitric oxide synthase expression contributes to myocardial dysfunction and higher mortality after myocardial infarction in mice. Circulation 104:700-704
11. Feng Q, Song W, Lu X, Hamilton J A, Lei M, Peng T, Yee S P (2002) Development of heart failure and congenital septal defects in mice lacking endothelial nitric oxide synthase. Circulation 106:873-879
12. Frampton J E (2010) Cetuximab: a review of its use in squamous cell carcinoma of the head and neck. Drugs 70:1987-2010
13. Gallagher G, Menzie S, Huang Y, Jackson C, Hunyor S N (2007) Regional cardiac dysfunction is associated with specific alterations in inflammatory cytokines and matrix metalloproteinases after acute myocardial infarction in sheep. Basic Res Cardiol 102:63-72
14. Garcia Arguinzonis M I, Galler A B, Walter U, Reinhard M, Simm A (2002) Increased spreading, Rac/p21-activated kinase (PAK) activity, and compromised cell motility in cells deficient in vasodilator-stimulated phosphoprotein (VASP). J Biol Chem 277:45604-45610
15. Hammoud L, Burger D E, Lu X, Feng Q (2009) Tissue inhibitor of metalloproteinase-3 inhibits neonatal mouse cardiomyocyte proliferation via EGFR/JNK/SP-1 signaling. Am J Physiol Cell Physiol 296:C735-C745
16. Hayashidani S, Tsutsui H, Ikeuchi M, Shiomi T, Matsusaka H, Kubota T, Imanaka-Yoshida K, Itoh T, Takeshita A (2003) Targeted deletion of MMP-2 attenuates early LV rupture and late remodeling after experimental myocardial infarction. Am J Physiol Heart Circ Physiol 285:H1229-H1235
17. Honan M B, Harrell F E, Jr., Reimer K A, Califf R M, Mark D B, Pryor D B, Hlatky M A (1990) Cardiac rupture, mortality and the timing of thrombolytic therapy: a meta-analysis. J Am Coll Cardiol 16:359-367
18. Kumegawa M, Hiramatsu M, Hatakeyama K, Yajima T, Kodama H, Osaki T, Kurisu K (1983) Effects of epidermal growth factor on osteoblastic cells in vitro. Calcif Tissue Int 35:542-548
19. Kurata S, Hata R (1991) Epidermal growth factor inhibits transcription of type I collagen genes and production of type I collagen in cultured human skin fibroblasts in the presence and absence of L-ascorbic acid 2-phosphate, a long-acting vitamin C derivative. J Biol Chem 266:9997-10003
20. Leask A (2007) TGFβ, cardiac fibroblasts, and the fibrotic response. Cardiovasc Res 74:207-212
21. Leask A, Abraham D J (2004) TGF-β signaling and the fibrotic response. FASEB J 18:816-827
22. Leco K J, Waterhouse P, Sanchez O H, Gowing K L, Poole A R, Wakeham A, Mak T W, Khokha R (2001) Spontaneous air space enlargement in the lungs of mice lacking tissue inhibitor of metalloproteinases-3 (TIMP-3). J Clin Invest 108:817-829
23. Lovelock J D, Baker A H, Gao F, Dong J F, Bergeron A L, McPheat W, Sivasubramanian N, Mann D L (2005) Heterogeneous effects of tissue inhibitors of matrix metalloproteinases on cardiac fibroblasts. Am J Physiol Heart Circ Physiol 288:H461-H468
24. Lu X, Hamilton J A, Shen J, Pang T, Jones D L, Potter R F, Arnold J M, Feng Q (2006) Role of tumor necrosis factor-alpha in myocardial dysfunction and apoptosis during hindlimb ischemia and reperfusion. Crit Care Med 34:484-491
25. Maelandsmo G M, Florenes V A, Nguyen M T, Flatmark K, Davidson B (2009) Different expression and clinical role of S100A4 in serous ovarian carcinoma at different anatomic sites. Tumour Biol 30:15-25
26. Peng T, Lu X, Feng Q (2005) Pivotal role of gp91phox-containing NADH oxidase in lipopolysaccharide-induced tumor necrosis factor-alpha expression and myocardial depression. Circulation 111:1637-1644
27. Peng T, Lu X, Lei M, Feng Q (2003) Endothelial nitric-oxide synthase enhances lipopolysaccharide-stimulated tumor necrosis factor-alpha expression via cAMP-mediated p38 MAPK pathway in cardiomyocytes. J Biol Chem 278:8099-8105
28. Pollak H, Nobis H, Mlczoch J (1994) Frequency of left ventricular free wall rupture complicating acute myocardial infarction since the advent of thrombolysis. Am J Cardiol 74:184-186
29. Rodriguez J, Viudez A, Ponz-Sarvise M, Gil-Aldea I, Chopitea A, Garcia-Foncillas J, Gil-Bazo I (2010) Improving disease control in advanced colorectal cancer: Panitumumab and cetuximab. Crit Rev Oncol Hematol 74:193-202
30. Sane D C, Mozingo W S, Becker R C (2009) Cardiac rupture after myocardial infarction: new insights from murine models. Cardiol Rev 17:293-299
31. Sun Y, Kiani M F, Postlethwaite A E, Weber K T (2002) Infarct scar as living tissue. Basic Res Cardiol 97:343-347
32. Tian H, Cimini M, Fedak P W, Altamentova S, Fazel S, Huang M L, Weisel R D, Li R K (2007) TIMP-3 deficiency accelerates cardiac remodeling after myocardial infarction. J Mol Cell Cardiol 43:733-743
33. Wang B, Omar A, Angelovska T, Drobic V, Rattan S G, Jones S C, Dixon I M (2007) Regulation of collagen synthesis by inhibitory Smad7 in cardiac myofibroblasts. Am J Physiol Heart Circ Physiol 293:H1282-H1290
34. Woessner J F, Jr. (1961) The determination of hydroxyproline in tissue and protein samples containing small proportions of this imino acid. Arch Biochem Biophys 93:440-447
35. Yang T T, Hawkes S P (1992) Role of the 21-kDa protein TIMP-3 in oncogenic transformation of cultured chicken embryo fibroblasts. Proc Natl Acad Sci USA 89:10676-10680
36. Zarzynska J, Gajewska M, Motyl T (2005) Effects of hormones and growth factors on TGF-beta1 expression in bovine mammary epithelial cells. J Dairy Res 72:39-48
37. Zhong H, Simons J W (1999) Direct comparison of GAPDH, beta-actin, cyclophilin, and 28S rRNA as internal standards for quantifying RNA levels under hypoxia. Biochem Biophys Res Commun 259:523-526
38. Bates R J, Beutler S, Resnekov L, Anagostopoulos C E. (1977) Cardiac Rupture-Challenge in Diagnosis and Management. Am J Cardiol. 40:429-37
39. Landmesser U. et. al. (2009) Potential novel pharmacological therapies for myocardial remodelling. Cardiovascular Research 81: 519-527
40. Kohler G, Milstein C. (1975) Continuous cultures of fused cells secreting antibody of predefined specificity. Nature 256: 495-497
41. Cole et al. (1985) Monoclonal Antibodies and Cancer Therapy, Alan R. Liss, Inc., pp. 77-96
42. Fire A, et al., (1998) Nature 391:806-811
43. Fire, A. (1999) Trends Genet. 15:358-363
44. Sharp P A. (2001) RNA interference. Genes Dev. 15:485-490
45. Hammond S M, et al. (2001) Nature Rev. Genet. 2:110-1119
46. Tuschl T. (2001) Chem. Biochem. 2:239-245
47. Hamilton A. et al. (1999) Science 286:950-952
48. Hammond S M. et al. (2000) Nature 404:293-296
49. Zamore P D. et al. (2000) Cell 101:25-33
50. Bernstein E, et al. (2001) Nature 409:363-366( )
51. Elbashir S M, et al. (2001) Genes Dev. 15: 188-200
52. Elbashir S M, et al. (2001) Nature 411:494-498
53. Rossini R, Senni M, Musumeci G, Ferrazzi P, Gavazzi A. (2010) Prevention of left ventricular remodeling after acute myocardial infarction: an update. Recent Pat Cardiovasc Drug Discov 5: 196-207
54. Maggioni A P, Maseri A, Fresco C, Franzosi M G, Mauri F, Santoro E, Tognoni G. (1993) Age-related increase in mortality among patients with first myocardial infarctions treated with thrombolysis. The Investigators of the Gruppo Italiano per lo Studio della Sopravvivenza nell'Infarto Miocardico (GISSI-2). N Engl J Med 329: 1442-1448
55. Hutchins K D, Skurnick J, Lavenhar M, Natarajan G A. (2002) Cardiac rupture in acute myocardial infarction: a reassessment. Am J Forensic Med Pathol 23:78-82
56. Fang L, Gao X M, Moore X L, Kiriazis H, Su Y, Ming Z, Lim Y L, Dart A M, Du X J (2007) Differences in inflammation, MMP activation and collagen damage account for gender difference in murine cardiac rupture following myocardial infarction. J Mol Cell Cardiol 43:535-544
57. Gao X M, Xu Q, Kiriazis H, Dart A M, Du X J (2005) Mouse model of post-infarct ventricular rupture: time course, strain- and gender-dependency, tensile strength, and histopathology. Cardiovasc Res 65:469-477

We claim:

1. A method of inhibiting cardiac rupture by increasing collagen synthesis in a heart of a human subject who suffered or is suffering myocardial infarction, the method comprising administering to the subject an epidermal growth factor receptor (EGFR) antagonist as a sole active agent, wherein the EGFR antagonist is selected from the group consisting of cetuximab, panitumumab, bevacizumab, zalutumumab, nimotuzumab or matuzumab.

2. The method of claim 1, wherein the subject is deficient in a tissue inhibitor of matrix metalloproteinase (TIMP).

3. The method of claim 2, wherein the TIMP is TIMP3.

4. The method of claim 1, wherein the EGFR antagonist is capable of inhibiting at least one EGFR-mediated biological activity.

5. The method of claim 1, wherein the EGFR antagonist is administered to the subject by injection.

6. The method of claim 1, wherein the EGFR antagonist is administered to the subject by liposome delivery.

7. The method of claim 1, wherein the EGFR antagonist is administered to the subject via an implantable device capable of sustained release of the EGFR antagonist.

8. A method of inducing wound healing by increasing collagen synthesis in the heart of a human subject that is healing from a myocardial infarction, said method comprising administering the subject an effective amount of an EGFR antagonist as a sole active agent, wherein the EGFR antagonist is selected from the group consisting of cetuximab, pinitumumab, bevacizumab, zalutumumab, nimotuzumab or matuzumab.

9. The method of claim 8, wherein the subject is deficient in a tissue inhibitor of matrix metalloproteinase (TIMP).

10. The method of claim 9, wherein the TIMP is TIMP3.

11. The method of claim 8, wherein the EGFR antagonist is an EGFR ligand variant capable of inhibiting at least one EGFR-mediated biological activity.

12. The method of claim 8, wherein the EGFR antagonist is administered to the subject by injection.

13. The method of claim 8, wherein the EGFR antagonist is administered to the subject by liposome delivery.

14. The method of claim 8, wherein the EGFR antagonist is administered to the subject via an implantable device capable of sustained release of the EGFR antagonist.

* * * * *